United States Patent [19]
Yeo

[11] Patent Number: 5,908,451
[45] Date of Patent: Jun. 1, 1999

[54] PROSTHETIC HEART VALVE

[75] Inventor: Joon Hock Yeo, Singapore, Singapore

[73] Assignee: Cardiotech International Corporation

[21] Appl. No.: 08/977,790

[22] Filed: Nov. 25, 1997

[51] Int. Cl.[6] .................................................. A61F 2/24
[52] U.S. Cl. ............................................................ 623/2
[58] Field of Search ........................................ 623/2, 900

[56] References Cited

U.S. PATENT DOCUMENTS

| | | | |
|---|---|---|---|
| 4,078,268 | 3/1978 | Possis | 623/2 |
| 4,373,216 | 2/1983 | Klawitter . | |
| 4,692,165 | 9/1987 | Bokros | 623/2 |
| 4,822,353 | 4/1989 | Bokros | 623/2 |
| 4,846,830 | 7/1989 | Knoch et al. | 623/2 |
| 5,171,263 | 12/1992 | Boyer et al. | 623/2 |
| 5,197,980 | 3/1993 | Gorshkov et al. | 623/2 |
| 5,354,330 | 10/1994 | Hanson et al. | 623/2 |
| 5,405,381 | 4/1995 | Olin | 623/2 |
| 5,545,216 | 8/1996 | Bokros et al. | 623/2 |

FOREIGN PATENT DOCUMENTS

| | | | |
|---|---|---|---|
| 97/05834 | 2/1997 | WIPO | 623/2 |

*Primary Examiner*—David H. Willse
*Attorney, Agent, or Firm*—Fitch, Even, Tabin & Flannery

[57] ABSTRACT

Bileaflet heart valves are illustrated which employ a pair of leaflets having flat inflow and outflow surfaces that are nonparallel to each other with the downstream arcuate edges being thinner than the mating upstream edges. The pivot mechanisms are constructed so that the leaflet inflow surfaces can be oriented parallel to the centerline through the valve body in the full open position, with the offset outflow surfaces constituting a diffuser section which provides for pressure recovery and reduces overall pressure drop through the valve. The pivot structures are preferably generally ellipsoidal in shape, with the long axis of the ellipsoid being aligned generally in an upstream-downstream direction. This feature together with the offset outflow surfaces of the leaflets promotes prompt closing of the valve. Optionally, upstream and downstream stops which protrude radially inward from the three-dimensional surfaces of the pivot structures can be offset with respect to the centers of the ellipsoidal structures to further promote prompt closing.

20 Claims, 3 Drawing Sheets

PROSTHETIC HEART VALVE

FIELD OF THE INVENTION

This invention relates to mechanical heart valves and more particularly to improved prosthetic heart valves having an annular valve body and a pair of leaflets which rotate on novel pivot supports and can assume orientations parallel to the centerline of the annular valve body in full open position.

BACKGROUND OF THE INVENTION

A wide range of mechanical heart valves have been developed as substitutes for diseased natural heart valves. These mechanical heart valves are essentially check valves which operate hemodynamically in synchronization with the pumping action of the heart, allowing blood flow in a downstream direction and blocking flow in the opposite or upstream direction. Such mechanical valves may employ a single valve member or occluder, a pair of occluders or leaflets, or three or more leaflets, which are appropriately supported for pivoting or both pivoting and translational movement within a surrounding, supporting valve body or housing. An important feature of all of these prosthetic heart valves is the pivot or hinge mechanism that is employed which allows prompt and smooth opening and closing movement of the occluders to repeatedly occur.

One of the largest selling mechanical heart valves in the United States is that marketed by St. Jude Medical, Inc. which is described in U.S. Pat. No. 4,276,658 (Jul. 7, 1981). This bileaflet mechanical heart valve incorporates a pivot mechanism which utilizes pairs of recesses formed in diametrically opposed flat wall surfaces in a tubular valve body which has an otherwise circular cross section. Each of the leaflets is provided with a pair of laterally extending protrusions or ears that are received in these recesses. The recesses have surfaces in the form of sections of a sphere which serve as bearing surfaces, with flat transverse walls of the recesses serving as guides to control the angles of maximal opening and of closing of the leaflets.

Since the issuance of this patent in 1981, there have been a large number of bileaflet heart valve designs which incorporate recesses of some type in walls of a valve housing to contain and control the pivoting action of a pair of leaflets having edges that mate in the closed position. However, potential clotting is a constant concern in the operation of any mechanical heart valve, and one disadvantage of such a recessed pivot mechanism is that adequate washing of the entire recess becomes a major concern because the tendency of the mainstream flow of blood through the valve body is to bypass such offset recess regions.

To avoid the potential disadvantage of having to assure constant adequate washing of such recesses, a number of mechanical heart valves were created which employed pivots in the form of posts, bumps or other protrusions which extended outward from the interior wall of the valve body and thus would be exposed to the mainstream flow of blood through the valve body. Such arrangements take advantage of a positive washing effect at the surfaces of the pivot mechanism during both opening and closing of the leaflets. Examples of mechanical heart valves of this general type are found in U.S. Pat. Nos. 4,692,165, 4,822,353, 4,863,467, 5,080,669, 5,197,980, 5,171,263, 5,405,381, 5,354,330, 5,116,367, 5,080,669, 4,863,459 and 4,373,216. The last-mentioned patent to Klawitter employs a pair of leaflets with notches formed in their lateral edges which are received about projections that extend radially inward from flat wall surfaces of the valved body and guide the pivoting movement of the leaflets. Bumps or protuberances in the otherwise flat walls serve as stops which assist in positioning leaflets in the open and closed positions.

The advantages of procuring good washing of the pivot mechanisms as a result of the elimination of such recesses comes not without some disadvantage, namely the projection of the pivot or hinge structure into the mainstream flow of blood causes some obstruction to overall blood flow through the valve in the open position. Many such pivot mechanisms have surfaces that are essentially transverse to the flow of blood and have the tendency to cause separation of blood flow; such is undesirable from the standpoint of increasing the pressure drop across the valve and creating turbulent shear from such flow separation, the result of which can be damage to blood cells as well as thrombosis or emboli generation.

As a result, improvements in heart valve construction have continued to be sought with the objective of creating mechanical valves having flow characteristics such that there is minimum resistance to blood flow and/or damage to blood in the open position, and also having the capability to close promptly upon the termination of the pumping stroke with only little regurgitation.

SUMMARY OF THE INVENTION

The present invention provides mechanical heart valves which exhibit the aforementioned desirable characteristics wherein a pair of valve leaflets are supported within an annular valve body having a bell-shaped entrance by means of notches in the lateral side edges thereof; these notches mate with novel supporting pivots that protrude from a pair of diametrically opposed flat surfaces in an otherwise circular cross section, valve body interior surface. The protruding pivots have convex surfaces which are of non-spherical three-dimensional curvature and have first and second stops associated therewith which protrude beyond these convex surfaces and assist in orienting the leaflets in the open and closed positions. The convex pivot surfaces are preferably generally ellipsoidal. These ellipsoidal pivots are oriented so that prompt rotation of the leaflets toward the closed position occurs as soon as backflow of blood through the valve begins even though the leaflets assume an orientation in the open position parallel to the valve centerline, and as a result, the amount of regurgitation is minimized.

The valve leaflets have flat inflow and outflow surfaces; however, these surfaces are not parallel to each other. The inflow surface is arbitrarily designated as the surface which faces upstream in the closed position. The planar leaflet surfaces are offset at an angle of between about 0.5° and about 4°, with the arcuate downstream edge of the leaflet being thinner than the straight upstream edge which mates with the corresponding upstream edge of the other leaflet in the closed position. The valve is designed so that the inflow surface of each leaflet will be parallel to the centerline in the open position, whereas the facing outflow surfaces of the leaflets form a diffusion section which offers pressure recovery as downstream flow exits the region of the leaflets. In addition, the center of gravity of the leaflets is shifted toward the pivot axis as a result of the tapering, and this shift lessens the impact at the instant of closing. Moreover, this construction has the dual advantage of (1) having the inflow surfaces aligned parallel to the centerline in the open position while the outflow surfaces afford some pressure recovery during periods of high downstream flow and (2) promoting prompt pivoting toward the closed position as soon as backflow of blood begins because of the offset of the tapered outflow surfaces.

DETAILED DESCRIPTION OF THE PREFERRED EMBODIMENTS

Illustrated in FIGS. 1–10 is a bileaflet heart valve 11 which is constructed so as to embody various features of the present invention. Heart valves having this illustrated construction are considered to exhibit improved blood flow, particularly when the valve is in its full open condition, as a result of the design and orientation of the leaflets and the construction of the entrance region of the valve body. The leaflets can align so that the inflow surfaces thereof are precisely parallel to the axial centerline through the valve body while the outflow surfaces that face each other create a channel which flares outward in a downstream direction and thus constitutes a diffuser section which affords pressure recovery. The bell mouth design of the entrance region of the valve body has a curvature such as to avoid boundary layer separation. Moreover, this particular curvature allows the curved entrance section to have an axial length that exceeds that of the downstream section, which is formed with generally rectilinear interior and exterior sidewalls. The provision of generally ellipsoidal pivots protruding from the interior walls of the valve body assures good washing at the locations of the pivot mechanisms, and the pivot design itself, as well as the nonparallel orientation of the outflow surfaces, assures rapid response in beginning closing movement upon the change in direction of blood flow.

Figure 5:
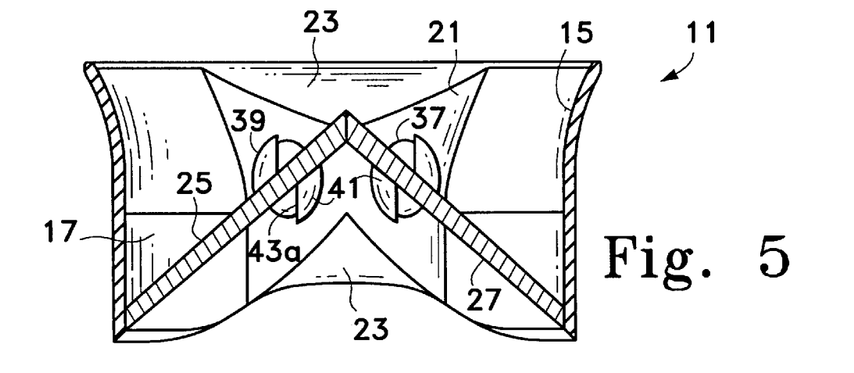
FIG. 5 is a sectional view similar to FIG. 3 with the leaflets shown in the closed position.

The illustrated heart valve 11 includes a tubular valve body 13 which has an entrance region 15 of bell-mouth shape and a downstream region 17 of generally rectilinear interior and exterior sidewalls. Supported within the valve body 13 are a pair of leaflets 19 which pivot about axes located in the entrance region. The leaflets 19, guided by pivot mechanisms to be described in detail hereinafter, alternately open to allow the smooth downstream flow of blood, as indicated by the arrow B in FIG. 3, and close, as shown in FIG. 5, to prevent any substantial backflow of blood, i.e. regurgitation. The valve body 13 defines a blood flow passageway having an axial centerline and is of general circular interior cross-section except for a pair of flat, parallel diametrically opposed sidewalls 21 which extend into both the entrance region 15 and the downstream region 17, and the valve body 13 may be provided with transitional regions 23 upstream and downstream of the flat sidewall sections. The interior surface of the downstream region 17 of the valve body is rectilinear except for the transitional regions 23; it is generally the surface of a right circular cylinder interrupted by the flat sidewalls 21. The downstream region 17 is considered to begin at the point of tangency between the bell mouth curve and the right circular cylindrical wall. The exterior surface of the downstream region is also rectilinear, except for any construction that might be provided to facilitate the attachment of a sewing ring. For example, a groove could be provided in the exterior surface to facilitate the attachment of a sewing ring as illustrated in U.S. Pat. No. 5,354,330, or a metal stiffening ring could be shrink-fit onto the exterior of the valve body for use in attaching a sewing ring, as generally described in U.S. Pat. No. 4,535,483.

The valve body 13 preferably has a scalloped downstream profile with a pair of shallow recesses 24 being formed in the contour of the valve body 13 in the regions just downstream of the flat wall sections 21. In a bileaflet valve of this type, such side openings provided by this scalloped construction are aligned with a central passageway region that is created between the leaflets 19. The valve body may be made of any suitable material, such as pyrocarbon or pyrocarbon-coated graphite as is well known in the art and, if so, the inclusion of a stiffening ring may be preferred. However, it should be understood that neither the materials nor the sewing ring construction are considered to form part of the present invention.

Figure 7:
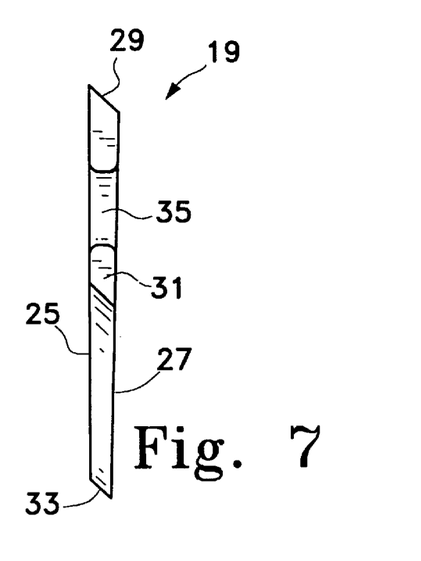
FIG. 7 is a left side elevation view of the leaflet shown in FIG. 6.

The leaflets 19 are identical in size and shape, and as best seen in FIG. 7, each leaflet has two rectilinear surfaces, which are preferably flat and which are referred to as an inflow surface 25 and an outflow surface 27, with the inflow surface being arbitrarily defined as the surface that faces upstream when the leaflets are in the closed position, as illustrated in FIG. 5. Although the leaflet surfaces are preferably flat, one or both of the surfaces could be slightly curved as shown, for example, in U.S. Pat. No. 5,246,453.

The leaflets 19 are formed with a straight upstream mating edge 29 which is aligned so as to seat flush against the corresponding mating edge surface in the closed position. Each leaflet also has a pair of flat lateral edges 31 and an arcuate major downstream edge 33. The flat lateral edges lie in juxtaposition with the flat sidewall sections 21 of the valve body, and the arcuate downstream edge 33 has a surface configuration such as to abut and lie relatively closely against the interior surface of the cylindrical sidewall of the downstream region 17 of the valve body. In the closed position configuration as seen in FIG. 5, the leaflets are oriented generally at an angle of about 55° and 35° to the centerline plane, i.e. the plane which contains the centerline of the tubular valve body and is perpendicular to the flat sidewalls 21. As should be apparent from FIG. 5, the alignment of the surfaces of the mating edges 29 and the inflow surfaces 25 is at the same angle of inclination.

The lateral edges 31 of the leaflets are formed with notches 35 which interengage with pivots 37 that protrude radially inward from the slot sidewall portions 21 of the valve body. The pivots 37 have surfaces of three-dimensional curvature which are preferably nonspherical and more preferably generally ellipsoidal. As perhaps best seen in FIGS. 8 and 10, the pivot 37 has a surface that is a section of an ellipsoid, the longer axis of which is aligned generally parallel to the centerline of the valve body and is the longer axis of the ellipse formed at the intersection with the plane of the flat sidewall 21. The following measurements with respect to dimensions of the pivot structure are generally referenced to the ellipse in the plane of the flat sidewall 21 from which the ellipsoid projects. Preferably, the pivot is constructed so that the long axis of the ellipsoid lies either in the plane of the flat sidewall or very close thereto, i.e. within a distance equal to about 10% of the length of the shortest axis of the ellipsoid, which is preferably lies perpendicular to the plane of the flat sidewall.

The preferred ellipsoid is defined as follows:

$$\frac{x^2}{a^2} + \frac{y^2}{b^2} + \frac{z^2}{c^2} = k$$

wherein a varies between about 0.5 to about 1, b varies between about 0.8 to about 1.3, and c varies between about 0.72 to about 1.24, and k is a constant, with the proviso that a, b and c are not all equal. Preferably, the shortest axis of the ellipsoid is the one which is aligned perpendicular to the sidewall, and it preferably has a length equal to between about 75% and about 95% of the shorter of the two other axes of the ellipsoid and is not longer than the shorter axis of the outline of the ellipse in the plane of the sidewall. Moreover, the intermediate length axis of the ellipsoid preferably has a length equal to between about 65% and about 85% of the length of the longest axis of this ellipsoid.

The pivots 37 and the axis of leaflet rotation are located in flat sidewall 21 in the entrance region 15 of the valve body which is particularly advantageous because it permits the valve to have a shorter overall axial length; in fact, the bell mouth curvature allows downstream region 17 to be shorter in axial length than the entrance section. As earlier indicated, the notches 35 in the lateral edges 31 of the leaflets 19 allow the leaflets to be journaled upon a pair of pivots 37 located in alignment with each other in the diametrically opposed flat sidewalls 21.

Figure 1:
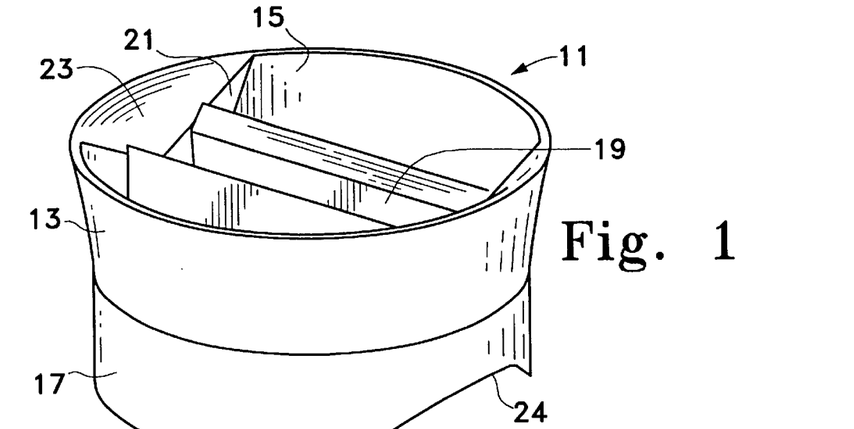
FIG. 1 is a perspective view of a bileaflet mechanical heart valve embodying various features of the present invention with the leaflets shown in the open position.
Figures 2, 3:
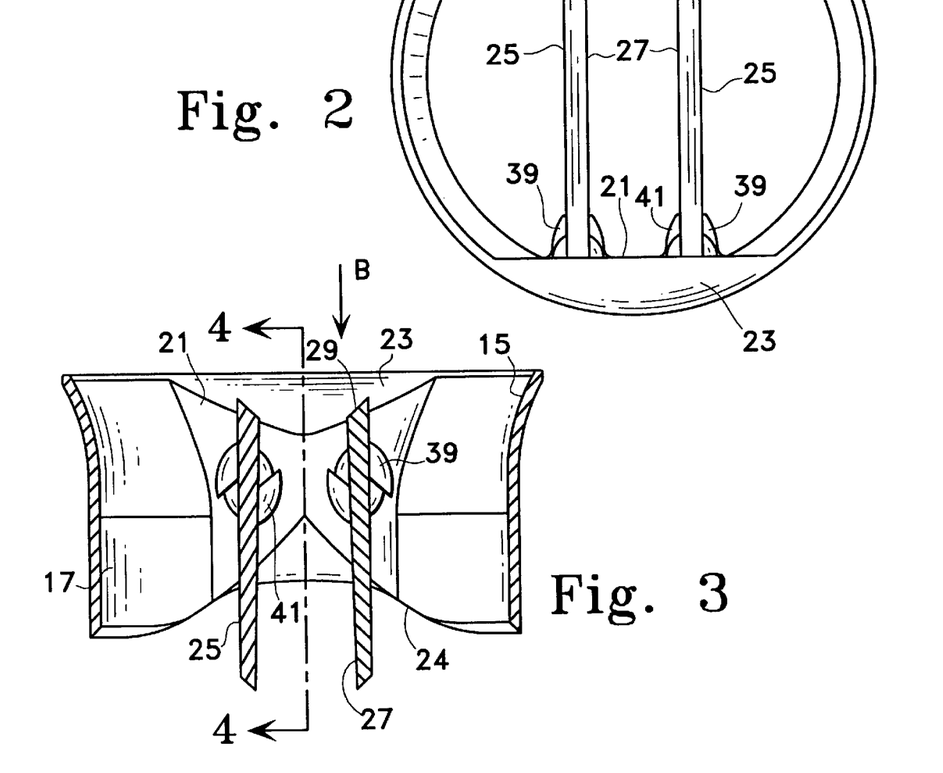
FIG. 2 is a top plan view of the heart valve shown in FIG. 1.
FIG. 3 is a sectional view taken generally along the line 3—3 of FIG. 2.
Figure 4:
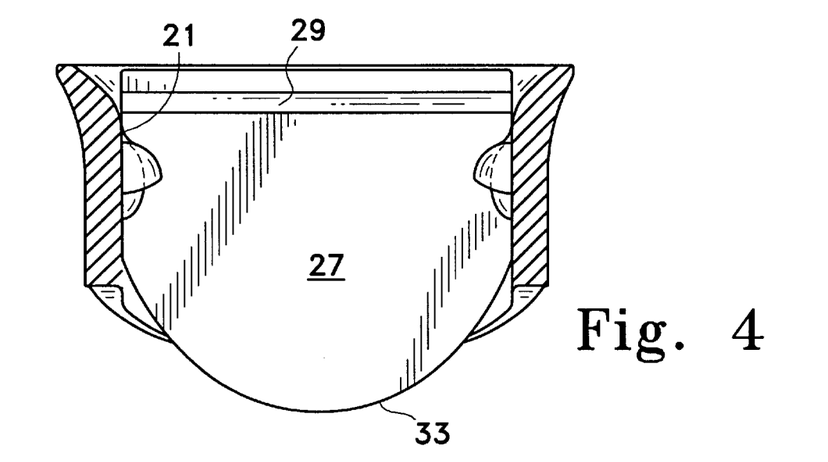
FIG. 4 is a sectional view of the valve taken generally along the line 4—4 of FIG. 3.
Figure 10:
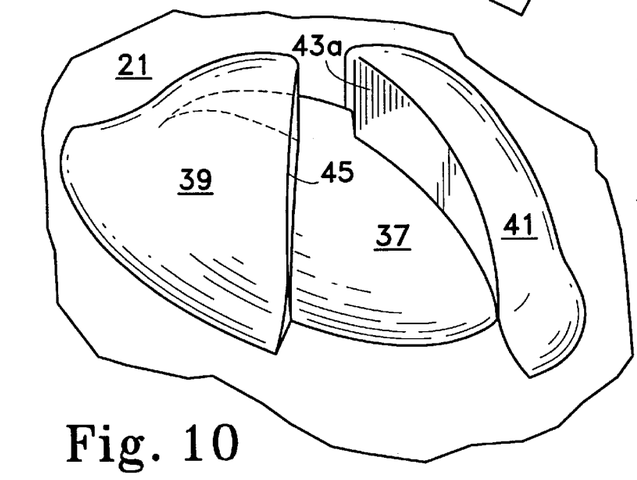
FIG. 10 is a fragmentary perspective view of the pivot illustrated in FIG. 8.

To define the open and closed positions of the leaflets, the pivots are constructed with first and second stops 39, 41 which extend radially into the flow passageway beyond the convex, nonspherical surfaces of the ellipsoidal pivots 37. As best seen in FIGS. 2 and 10, the first and second stops have curved end surfaces which generally follow the curvature of the threedimensional surface of the pivots, and each stop is provided with one wall that is oriented to lie in juxtaposition of the leaflet in the open position and another to so lie in the closed position. The stops 39 that are located the further upstream are referred to as the first or upstream stops, and the other stops 41 that are located further downstream on each pivot are referred to as the second or downstream stops.

Figures 8, 9, 11, 12:
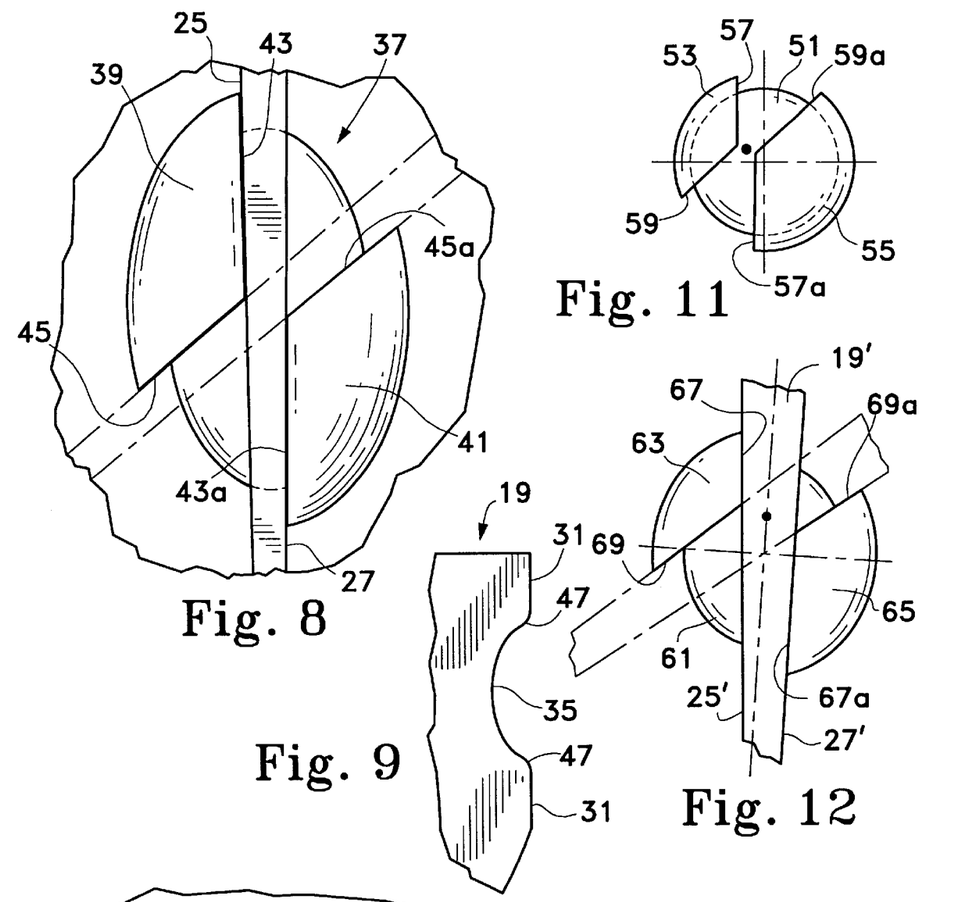
FIG. 8 is a fragmentary view, enlarged in size, of the left-hand pivot structure of the valve body shown in FIG. 3, with the leaflet shown in ghost outline in its open position.
FIG. 9 is an enlarged fragmentary elevation view, enlarged in size, of the right-hand lateral edge portion of the leaflet shown in FIG. 6.
FIG. 11 is a fragmentary view similar to FIG. 8 showing an alternative embodiment of a pivot mechanism where the axis of leaflet rotation is offset from the centerpoint of the pivot structure.
FIGS. 12 and 13 are fragmentary enlarged views similar to FIG. 11 showing two further alternative embodiments of pivot structures constructed so that the axis of leaflet rotation will be offset from the centerpoint of the ellipsoidal pivot structure.

As best seen in FIG. 8, the first stop 39 is provided with a wall 43 which determines the orientation of the leaflet in the full open position. The open position wall 43 is oriented so that the inflow surface of the leaflet will abut against this wall when the leaflet 19 is in the full open position. The downstream stops 41 each have a complementary wall 43a against which the outflow surface 27 of the leaflet will abut in the open position. Each upstream stop 39 also has a closed position wall 45 along which the inflow surface of the leaflet will lie in juxtaposition in the closed position, and the downstream stops 41 have complementary walls 45a along which the outflow surface 27 of the leaflet will lie in juxtaposition. As best seen in FIG. 9, the notches 35 of the leaflets 19 are proportioned to lie in juxtaposition with the surface of the ellipsoidal pivot 37 in the full open position. The edges where the notches meet the lateral edges 31 of the leaflets are rounded at 47, and as shown in FIG. 7, the wall surface which defines the notches 35 is also slightly rounded. Preferably, the edge surface of the notch 35 as seen in FIG. 7 has a radius of curvature between about one-half and twice the thickness of the leaflet 17 at the notch.

As previously indicated, the inflow and outflow surfaces of the leaflets 19 are preferably flat but are not parallel to each other. The two surfaces should be offset from a parallel orientation at an angle between about 0.5° and about 4°, and more preferably at an angle of between about 2° and about 3.5°, with the leaflets being thicker at the upstream mating edges 29 than at the downstream arcuate edges 33. Taking into consideration the nonparallel orientation of the inflow and outflow surfaces of the leaflets, the valve is constructed so that the upstream and downstream stops allow the leaflet inflow surfaces 25 to assume an orientation parallel to each other and to the flow of passageway centerline in the open position, as defined by the open position walls 43 and 43a. Therefore, the walls 43, against which the inflow surfaces abut, are oriented parallel to the centerline, and the stops 43a against which the outflow surfaces abut are oriented at a slight offset thereto, equal to the offset between the opposite surfaces of the leaflets. A similar relationship applies between the closed position walls 45 on the upstream stops 39 and the walls 45a on the downstream stops 41, i.e. again being offset from a parallel orientation to each other by the same number of degrees.

As can be seen from FIG. 8, each of the stops 39, 41 is provided with a pair of walls which are arranged at an angle to each other of greater than 90° and which angle is preferably between about 115° and about 135°. The alignment of the stops 39, 41 is such that the axis of rotation of the leaflet will be generally along the centers of the two ellipsoids. In the open position, the inflow surfaces will abut the walls 43, and the outflow surface will abut the walls 43a. In the closed position, the mating edges 29 of the two leaflets abut and the arcuate downstream edges 33 abut the interior generally cylindrical surfaces of the downstream region 17 of the valve body in the region of the scallops. The inflow and outflow surfaces abut or lie in juxtaposition with the walls 45 and 45a, respectively, depending upon the tolerances in leaflet construction. The alignment of the ellipsoidal pivots 37 can be slightly varied so long as its long axis is aligned close to the upstream-downstream direction. For example, the pivots 37 may be aligned so that the long axis is parallel to the wall 43 and thus to the centerline of the valve body 13. Alternatively, the pivots 37 may be aligned so that the long axis is parallel to the walls 43a, which are offset from the walls 43 that are parallel to the valve centerline. Although either of these is preferred, further slight offsets in either angular direction are also acceptable.

One of the advantages of the valve structure is that, in the full open position, the inflow surfaces 25 are aligned perfectly parallel to the centerline of the valve body 13, and thus create minimal disruption of blood flow therethrough. At the same time, the outflow surfaces 27 form a central channel which diffuses outwardly in a downstream direction, and this diffusion section aids in pressure recovery and lowers the overall pressure drop across the valve 11.

Figure 6:
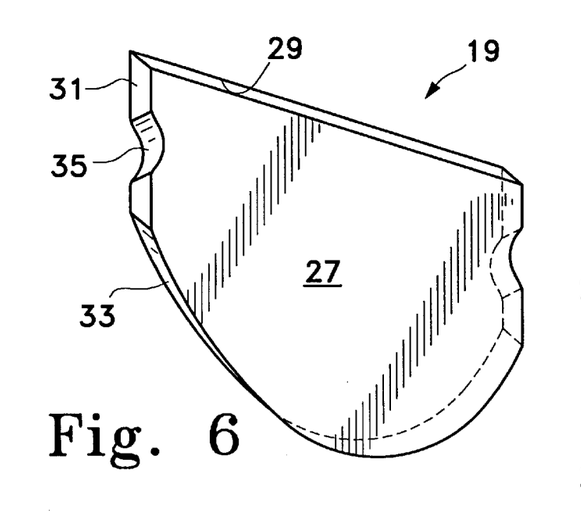
FIG. 6 is a perspective view, enlarged in size, of one of the leaflets in the valve of FIGS. 1 through 5.

In addition, however, the nonparallel orientation also has an advantage at the time of flow reversal when it becomes important that the valve close as quickly as possible to minimize regurgitation. In this respect, the offset of the outflow surfaces 27 from the inflow surfaces 25 that are parallel to the centerline provides an immediate force vector urging the leaflets 19 toward the closed position when backflow of blood begins, and this force vector in cooperation with the ellipsoidal pivots assures prompt closing. As best seen perhaps from FIG. 8, the drag upon the leaflets 19 by the backflowing blood (in this figure such backflow will be upward) will cause the downstream portion of the curved edge that defines the notch 35 to be forced against the three-dimensionally curved surface of the ellipsoidal pivot 37. Because the ellipsoidal surface falls away in the segment between the wall 43 and the wall 45 of the stops 41, 39, this promotes prompt closing action; likewise, there is adequate clearance along the upstream section of the notch 35 so as to not hinder closing pivoting movement. Once both leaflets 19 reach the closed position, the mating edges 29 will abut when the downstream edges 33 become seated against the interior wall of the valve body, and there will generally be clearance between the notch 35 and the pivots 37 in the full closed position. This clearance assures there will be sufficient leakage to assure good washing of the pivot mechanism so as to positively avert any potential clotting in this region. Upon the reversal of flow on the next pumping stroke of the heart for example, the valve opens easily because of the force against the large surface region of the leaflet inflow surface 25 lying downstream from the notches, as best seen in FIG. 6, causes the leaflets to pivot back to the full open position with the notches 35 riding along the three-dimensionally curved surface of the pivots 37.

Figure 13:
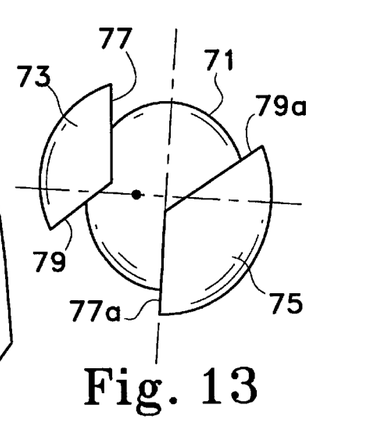

Shown in FIGS. 11, 12 and 13 are alternative embodiments of pivot structures where the upstream and downstream stops are offset with regard to the center of the three-dimensional body that forms the pivot surface. By offset is meant that, if a line is drawn between the centers of the two bodies which constitute the surfaces of the pivots, which line would be perpendicular to the planes of the flat sidewalls 21 of the valve body, the upstream and downstream stops would not be centered about this connecting line. This is in contrast to the structure depicted for example in FIG. 8 wherein the nominal axis of rotation of the leaflet 19 will be about a line that coincides with the centerpoints of the two ellipsoidal surfaces that form the pivot structures 37.

Although the pivot structures preferably have a three-dimensional surface of nonspherical configuration, as shown in FIG. 11, a spherical pivot 51 having offset upstream and downstream stops may be employed. When such an offset arrangement is employed, it is preferred that the offset is in an upstream direction from the central axis between the two pivot structure surfaces. One such example is shown in FIG. 11 where the pivot structure 51 is depicted having a spherical surface with upstream stops 53 and downstream stops 55. Walls 57 and 57a will lie in juxtaposition with the leaflet inflow surfaces and the outflow surfaces, respectively, in the full open position, and the walls 59 and 59a will lie in juxtaposition with the inflow and outflow surfaces of the leaflet, respectively, in the closed position. One will notice that, as a result of this offset, the size of the upstream stop 53 becomes somewhat smaller than the size of the downstream stop 55.

FIG. 12 illustrates a similar offset arrangement incorporated into an ellipsoidal pivot structure 61. Again, the upstream stops 63 are smaller than the downstream stops 65. In this particular embodiment, the long axis of the ellipsoid is aligned with the wall 67a that constitutes the open position stop for the outflow surface 27' of a leaflet 19'. The wall 67 remains parallel to the centerline through the valve body so that the inflow surface 25' of the leaflet is aligned parallel thereto in the full open position. The walls 69 and 69a, which lie in juxtaposition with the inflow and outflow surfaces, respectively, are similarly positioned as previously described.

Illustrated in FIG. 13 is another alternative embodiment of an ellipsoidal pivot 71 where, instead of the offset being upstream and away from the valve centerline, the offset is only in a direction away from the centerline of the valve body. In this pivot structure 71, upstream stops 73 are likewise smaller in dimension than downstream stops 75, and the alignment of the ellipsoid is such that its long axis lies in the plane of the wall 77a that serves as the open position stop for the leaflet outflow surface and so that the wall 77, which is aligned parallel with the centerline through the valve body, is offset from the long axis. The alignment of the walls 79 and 79a is as previously indicated.

The advantage in offsetting the pivot axis of the leaflet from the centerline through the three-dimensionally curved surface of the pivot structure is that the center of rotation of the leaflet, as depicted by the black dots, is displaced away from what would be the center of the circle or the ellipse, as shown in FIGS. 11, 12 and 13. As a result of this displacement the leaflet is now riding or sliding on a more exaggerated slope, i.e. a slope of greater angular degree, during the closing movement. Because of the greater the slope, there is greater tendency to travel down and across this slope, and such arrangement assists in initiating the prompt closing movement from the full open position.

As a result of such an offset, a difference in the size of the stops results so long as the stops are constructed having three-dimensionally curved end surfaces that generally follow the curvature of the pivot structures upon which these stops are superimposed. However, another way of viewing the result of the offset is with reference to the alignment of the three-dimensional surface of the pivots 37. In the pivots 37, the potential bearing surface between the walls 43 and 45a is the same as that between the walls 45 and 43a. In contrast, the curved region surface area that lies spatially between the pair of upstream walls 57 and 59a is substantially less than the surface area between the downstream walls 59 and 57a, as can be seen from FIGS. 11, 12 and 13.

Although the invention has been described in terms of the preferred embodiments which constitute the best mode presently contemplated by the inventor, it should be understood that changes and modifications as would be obvious to one having the ordinary skill in this art may be made without departing from the scope of the invention which is defined by the claims appended hereto. For example, although pyrocarbon is the preferred material for manufacturing the components of these heart valves, other biocompatible materials as are sometimes employed in prostheses may alternatively be used. Any suitable sewing ring can be affixed to the exterior surface of the valve body to permit it to be sutured in place within a patient, and the sewing ring structure forms no part of the present invention.

Particular features are emphasized in the claims which follow.

What is claimed is:

1. A prosthetic heart valve for controlling blood flow in association with a chamber of the human heart, which valve comprises:

an annular valve body of generally circular interior cross-section except for a pair of flat, parallel diametrically opposed sidewalls, which valve body provides a passageway about a centerline for blood flow from upstream to downstream therethrough, convex pivot means protruding into said flow passageway from each of said flat sidewalls, and two leaflets designed to rotate about said pivot means so as to allow downstream blood flow when in an open position and to prevent any substantial upstream blood flow when in a closed position, said leaflets having upstream, downstream and lateral edges and having opposite planar inflow and outflow major surfaces, with said inflow surfaces facing upstream in the closed position, and said leaflets also having notch means along said lateral edges for interengaging with said pivot means, said planar inflow and outflow surfaces being nonparallel and offset from a parallel orientation at an angle of between about 0.5° and about 4°, with said leaflet upstream edge being thicker than said downstream edge, said pivot means comprising two convex pivots protruding from each of said flat sidewalls, with said pivots being arranged in pairs and with each said pair of pivots respectively interengaging with said notch means in said lateral edges of one of said leaflets, each of said pivots having first and second stops associated therewith which extend into said flow passageway beyond said convex surfaces, each said first stop having wall means that is located to lie in juxtaposition with a region adjacent said notch means of said inflow surface of one said leaflet when said leaflet is in the closed position, and each said second stop each having wall means that is located to lie in juxtaposition with a region of said outflow surface of said one leaflet when said leaflet is in the open position, and said second stop being so located that, in a full open position, said planar inflow surfaces are essentially parallel to said centerline and said planar outflow surfaces diverge from each other in a downstream direction and thereby reduce pressure drop across the heart valve.

2. The heart valve according to claim 1 wherein said valve body has (a) an upstream entrance region which is formed to have a bell mouth design which is curved so as to avoid boundary layer separation at a location where downstream flowing blood enters said valve body and (b) a downstream region having a generally rectilinear interior sidewall, the diameter of the exterior of said valve body at its upstream end being between about 5% and about 30% greater than its interior diameter at its downstream end, the axial length of said entrance region being greater than the axial length of said downstream region, the radius of curvature of said curved entrance region being between about 0.8 and about 2.8 times the axial length of said valve body, and the axes about which said leaflets pivot being located in said entrance region of said valve body.

3. A prosthetic heart valve for controlling blood flow in association with a chamber of the human heart, which valve comprises:

an annular valve body of generally circular interior cross-section except for a pair of flat, parallel diametrically opposed sidewalls, which valve body provides a passageway about a centerline for blood flow from upstream to downstream therethrough, convex pivot means protruding into said flow passageway from each of said flat sidewalls, and two leaflets designed to rotate about said pivot means so as to allow downstream blood flow when in an open position and to prevent any substantial upstream blood flow when in a closed position, said leaflets having upstream, downstream and lateral edges and having opposite inflow and outflow major surfaces, with said inflow surfaces facing upstream in the closed position, and said leaflets also having notch means along each of said lateral edges for interengaging with said pivot means, said pivot means comprising two convex pivots protruding from each of said flat sidewalls, said convex pivots being arranged in pairs and with each said pair of pivots respectively interengaging with said notch means in said lateral edges of one of said leaflets, and said convex pivots each having a surface of three-dimensional curvature, each of said convex pivots having first and second stops associated therewith which extend from said convex surface into said flow passageway, each said first stop having wall means that is located to lie in juxtaposition to a region of said inflow surface of one said leaflet, at a location adjacent said notch means, when said leaflet is in the closed position, and each said second stop having wall means that is located to lie in juxtaposition with a region of said outflow surface of said one leaflet when said leaflet is in the open position, and said stops being located nonsymmetrically relative to a center of said three-dimensionally curved surface of said convex pivot so that said leaflets rotate about axes which are so offset from said center of said three-dimensionally curved surface that, during closing movement of said leaflets, said notch means thereof are sliding along sections of said three-dimensionally curved surface having a slope of increasing angular degree in the direction of closing rotation.

4. The heart valve of claim 3 wherein said pivot surface is spheroidal and said axis of leaflet rotation is offset upstream and in a direction away from the valve centerline with respect to a line through the center of said spheroidal surface that is perpendicular to said flat sidewall.

5. The heart valve of claim 3 wherein said pivot surface is generally ellipsoidal and said axis is offset upstream and in a direction away from the valve centerline from a line through the center of said generally ellipsoidal surface that is perpendicular to said flat sidewall.

6. A prosthetic heart valve for controlling blood flow in association with a chamber of the human heart, which valve comprises:

an annular valve body of generally circular interior cross-section except for a pair of flat, parallel diametrically opposed sidewalls, which valve body provides a passageway about a centerline for blood flow from upstream to downstream therethrough, convex pivot means protruding into said flow passageway from each of said flat sidewalls, and two leaflets designed to rotate about said pivot means so as to allow downstream blood flow when in an open position and to prevent any substantial upstream blood flow when in a closed position, said leaflets having upstream, downstream and lateral edges and having opposite inflow and outflow major surfaces, with said inflow surfaces facing upstream in the closed position, and said leaflets also having notch means along each of said lateral edges for interengaging with said pivot means, said pivot means comprising two convex pivots protruding from each of said flat sidewalls, said convex pivots being arranged in pairs and with each said pair of pivots respectively interengaging with said notch means in said lateral edges of one of said leaflets, and said convex pivots each having a surface of three-dimensional curvature that is generally ellipsoidal, each of said convex pivots having first and second stops associated therewith which include a pair of flat walls arranged at an angle to each other of greater than 90° and which extend into said flow passageway beyond said convex surfaces, each said first stop having one said flat wall that is located to lie in juxtaposition to a region of said inflow surface of one said leaflet at a location adjacent said notch means when said leaflet is in the closed position, and each said second stop each having one said flat wall that is located to lie in juxtaposition with a region of said outflow surface of said one leaflet when said leaflet is in the open position.

7. The heart valve according to claim 6 wherein said flat walls of both said stops are oriented to each other at about the same angle, which angle is between about 115° and about 135°.

8. The heart valve according to claim 6 wherein one of said two stops which protrude from said convex surface is located closer than the other to a plane that is perpendicular to said flat sidewall of said valve body and includes the central axis of said generally ellipsoidal surface.

9. A prosthetic heart valve for controlling blood flow in association with a chamber of the human heart, which valve comprises:

an annular valve body of generally circular interior cross-section except for a pair of flat, parallel diametrically opposed sidewalls, which valve body provides a passageway about a centerline for blood flow from upstream to downstream therethrough, convex pivot means protruding into said flow passageway from each of said flat sidewalls, and two leaflets designed to rotate about said pivot means so as to allow downstream blood flow when in an open position and to prevent any substantial upstream blood flow when in a closed position, said leaflets having upstream, downstream and lateral edges and having opposite inflow and outflow major surfaces, with said inflow surfaces facing upstream in the closed position, and said leaflets also having notch means along each of said lateral edges for interengaging with said pivot means, said pivot means comprising two convex pivots protruding from each of said flat sidewalls, said convex pivots being arranged in pairs and with each said pair of pivots respectively interengaging with said notch means in said lateral edges of one of said leaflets, and said convex pivots each having a nonspherical surface of three-dimensional curvature that has a dimension in the upstream-downstream direction which is at least about 30% greater than a maximum dimension of said nonspherical surface in a transverse direction, each of said convex pivots having first and second stops associated therewith which extend into said flow passageway beyond said convex nonspherical surfaces, each said first stop having wall means that is located to lie in juxtaposition to a region of said inflow surface of one said leaflet, at a location adjacent said notch means, when said leaflet is in the closed position, and each said second stop each having wall means that is located to lie in juxtaposition with a region of said outflow surface of said one leaflet when said leaflet is in the open position.

10. The heart valve according to claim 9 wherein said notch means has an edge surface which is proportioned to generally register with the curvature of a region of said convex pivot with which it is in juxtaposition in a full open position.

11. The heart valve according to claim 10 wherein said edge surface of said notch means has a radius of curvature between about one-half and twice the thickness of said leaflet at said notch means.

12. A prosthetic heart valve for controlling blood flow in association with a chamber of the human heart, which valve comprises:

an annular valve body of generally circular interior cross-section except for a pair of flat, parallel diametrically opposed sidewalls, which valve body provides a passageway about a centerline for blood flow from upstream to downstream therethrough, convex pivot means protruding into said flow passageway from each of said flat sidewalls, and two leaflets designed to rotate about said pivot means so as to allow downstream blood flow when in an open position and to prevent any substantial upstream blood flow when in a closed position, said leaflets having upstream, downstream and lateral edges and having opposite inflow and outflow major surfaces, with said inflow surfaces facing upstream in the closed position, and said leaflets also having notch means along each of said lateral edges for interengaging with said pivot means, said pivot means comprising two convex pivots protruding from each of said flat sidewalls, said convex pivots being arranged in pairs and with each said pair of pivots respectively interengaging with said notch means in said lateral edges of one of said leaflets, and said convex pivots each having a surface of three-dimensional curvature that is generally ellipsoidal, each of said convex pivots having first and second stops associated therewith which extend into said flow passageway beyond said convex surfaces, each said first stop having wall means that is located to lie in juxtaposition to a region of said inflow surface of one said leaflet, at a location adjacent said notch means, when said leaflet is in the closed position, and each said second stop each having wall means that is located to lie in juxtaposition with a region of said outflow surface of said one leaflet when said leaflet is in the open position.

13. The heart valve according to claim 12 wherein said convex pivot surfaces are surfaces of a section of either an ellipsoid or an ellipse of revolution about its longer axis.

14. The heart valve according to claim 12 wherein said convex nonspherical surfaces are surfaces of an ellipsoid defined by the formula:

$$\frac{x^2}{a^2} + \frac{y^2}{b^2} + \frac{z^2}{c^2} = k$$

wherein a varies between about 0.5 to about 1, b varies between about 0.8 to about 1.3, and c varies between about 0.72 to about 1.24, and k is a constant, with the proviso that a, b and c are not all equal.

15. A prosthetic heart valve for controlling blood flow in association with a chamber of the human heart, which valve comprises:

an annular valve body of generally circular interior cross-section except for a pair of flat, parallel diametrically opposed sidewalls, which valve body provides a passageway about a centerline for blood flow from upstream to downstream therethrough, convex pivot means protruding into said flow passageway from each of said flat sidewalls, and two leaflets designed to rotate about said pivot means so as to allow downstream blood flow when in an open position and to prevent any substantial upstream blood flow when in the closed position, said leaflets having upstream, downstream and lateral edges and having opposite inflow and outflow planar surfaces, with said inflow surfaces facing upstream in the closed position and with said planar inflow and outflow surfaces being offset at an angle between about 0.5° and about 4° from a parallel orientation to each other, and said leaflets also having notch means along each of said lateral edges for interengaging with said pivot means, said pivot means comprising two convex pivots protruding from each of said flat sidewalls, said convex pivots being arranged in pairs and with each said pair of pivots respectively interengaging with said notch means in said lateral edges of one of said leaflets, and said convex pivots each having a surface of three-dimensional curvature that is nonspherical, each of said convex pivots having first and second stops associated therewith which extend into said flow passageway beyond said convex nonspherical surfaces, each said first stop having wall means that is located to lie in juxtaposition to a region of said inflow surface of one said leaflet, at a location adjacent said notch means, when said leaflet is in the closed position, and each said second stop each having wall means that is located to lie in juxtaposition with a region of said outflow surface of said one leaflet when said leaflet is in the open position.

16. The heart valve according to claim 15 wherein said planar inflow and outflow surfaces are offset from a parallel orientation by an angle of between about 2° and about 3.5° and wherein said leaflets are thicker at said upstream edges as compared to said downstream edges.

17. The heart valve according to claim 15 wherein said first and second stops protrude outward from and interrupt said convex pivot surfaces, wherein said first stops extend upstream of said second stops and wherein said leaflet outflow surfaces in the full open position abut flat surfaces on said second stops which are positioned to allow said leaflet inflow surfaces to assume a orientation parallel to each other and to said flow passageway centerline.

18. The heart valve according to claim 17 wherein said thicker upstream edges of said leaflets are formed with edge surfaces that are oriented at an angle to said leaflet inflow surfaces such that said upstream edge surfaces of said two leaflets lie in surface-to-surface contact with each other when said leaflets are in the closed position, and wherein, in the closed position, said leaflet inflow surfaces are oriented at an angle of between about 30° and about 45° to a plane that is perpendicular to the centerline of the valve flow passageway.

19. The heart valve according to claim 15 wherein said valve body has (a) an upstream entrance region which is formed to have a bell mouth design which is curved so as to avoid boundary layer separation at a location where downstream flowing blood enters said valve body and (b) a downstream region having a generally rectilinear interior sidewall, the diameter of the exterior of said valve body at its upstream end being between about 5% and about 30% greater than its interior diameter at its downstream end, the axial length of said entrance region being greater than the axial length of said downstream region, the radius of curvature of said curved entrance region being between about 0.8 and about 2.8 times the axial length of said valve body, and the axes about which said leaflets pivot being located in said entrance region of said valve body.

20. The heart valve according to claim 19 wherein said valve body is formed with two diametrically opposed concave scallops in the downstream edge thereof in regions generally in alignment with said parallel flat sidewalls.

* * * * *